United States Patent
Eliseev

(10) Patent No.: US 9,833,467 B2
(45) Date of Patent: Dec. 5, 2017

(54) USE OF CYCLOPHILIN D INHIBITORS TO TREAT OR PREVENT BONE DISORDERS

(71) Applicant: UNIVERSITY OF ROCHESTER, Rochester, NY (US)

(72) Inventor: Roman A. Eliseev, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 14/651,963

(22) PCT Filed: Dec. 12, 2013

(86) PCT No.: PCT/US2013/074685
§ 371 (c)(1),
(2) Date: Jun. 12, 2015

(87) PCT Pub. No.: WO2014/093632
PCT Pub. Date: Jun. 19, 2014

(65) Prior Publication Data
US 2015/0320828 A1    Nov. 12, 2015

Related U.S. Application Data

(60) Provisional application No. 61/736,072, filed on Dec. 12, 2012.

(51) Int. Cl.
*A61P 19/00*    (2006.01)
*A61K 31/7105*  (2006.01)
*A61K 38/13*    (2006.01)
*A61K 35/28*    (2015.01)

(52) U.S. Cl.
CPC .......... *A61K 31/7105* (2013.01); *A61K 35/28* (2013.01); *A61K 38/13* (2013.01)

(58) Field of Classification Search
USPC .......... 424/93.21; 514/1, 2, 16.7, 16.8, 16.9
See application file for complete search history.

(56) References Cited

PUBLICATIONS

Kohjima et al, Liver Internal ISSN, pp. 1273-1281 (2007).*
Guo et al, Acta Pharmacologica Sinica, vol. 10, pp. 1201-1211 (2005).*
Chen et al, Stem Cells, vol. 26, pp. 960-968 (2008).*
Pietila et al, Tissue Engineering, Part C, vol. 16, No. 3, pp. 435-445 (2010).*
PCT/US2013/074685, "International Search Report and Written Opinion", dated Feb. 28, 2014, 6 pages.
PCT/US2013/074685, "International Preliminary Report on Patentability", dated Jun. 25, 2015, 6 pages.
Bernardi, P.; "Mitochondrial Transport of Cations: Channels, Exchangers, and Permeability Transition"; Physiological Reviews, 1999 79: 1127-1155.
Bernardi et al., "Mitochondria and Cell Death", Eur. J. Biochem; 1999; 264: 687-701.
Bianco et al. "The meaning, the sense and the significance: translating the science of mesenchymal stem cells into medicine" Nature Medicine, 2013, 19, 35-42.
Bielby, et al., "The Role of Mesenchymal Stem Cells in Maintenance and Repair of Bone"; Injury, 2007; 38: S26-S32.
Chen et al., "Coordinated Changes of Mitochondrial Biogenesis and Antioxidant Enzymes During Osteogenic Differentiation of Human Mesenchymal Stem Cells"; Stem Cells, 2008; 26: 960-968.
Chen et al., Upregulation of Mitochondrial Function and Antioxidant Defense in the Differentiation of Stem Cells; Biochimica et Biophysica Acta, 2010; 1800: 257-263.
Duque, G. "Bone and Fat Connection in Aging Bone"; Current Opinion in Rheumatology, 2008; 20: 429-434.
Dy et al., "Sex and Gender Considerations in Male Patients with Osteoporosis"; Clin. Orthop. Relat. Res., 2011; 469:1906-1912.
Guo et al. "Novel cyclophilin D inhibitors derived from quinoxaline exhibit highly inhibitory activity against rat mitochondrial swelling and $Ca^{2+}$ uptake/release"Acta Pharmacologica Sinica, 2005, 26: 1201-1211.
Gruber et al., "Osteoblast Numbers After Calcitonin Therapy: A Retrospective Study of Paired Biopsies Obtained During Long-Term Calcitonin Therapy in Postmenopausal Osteoporosis" Calcif Tissue Int, 2000, 66:29-34.
He et al., "Regulated and Unregulated Mitochondrial Permeability Transition Pores: a New Paradigm of Pore Structure and Function?" FEBS Letters, 2002; 512:1-7.
Kolf, et al., "Biology of Adult Mesenchymal Stem Cells: Regulation of Niche, Self-Renewal and Differentiation"; Arthritis Research and Therapy, 2007; 9: 204-214.
Manolagas, SC "Birth and Death of Bone Cells: Basic Regulatory Mechanisms and Implicaitons for the Pathogenesis and Treatment of Osteoporosis"; Endocrine Reviews, 2000; 21: 115-137.
Manolagas et al., "Sex Steroids and Bone"; Recent Progress in Hormone Research, 2002; 57: 385-409.
Pattappa et al., The Metabolism of Human Mesenchymal Stem Cells During Proliferation and Differentiation; J. Cell. Phys., 2011; 226: 2562-2570.
Pietila et al., "Mitochondrial Function Determines the Viability and Osteogenic Potency of Human Mesenchymal Stem Cells"; Tissue Engineering Part C: Methods, 2009; 16: 435-445.
Rasola et al., "The Mitochondrial Permeability Transition Pore and its Involvement in Cell Death and in Disease Pathogenesis", Apoptosis; 2007;12: 815-833.
Sastre et al., "The Role of Mitochondrial Oxidative Stress in Aging", Free Radical Biology and Medicine; 2003; 35: 1-8.
Shapovalov et al., "Mitochondrial dysfunction in cancer cells due to aberrant mitochondrial replication", J Biol Chem., 2011, 286:22331-8.
Unnanuntana et al., "Diseases affecting bone quality: Beyond Osteoporosis"; Clin. Orthop. Relat. Res., 2011; 469: 2194-2206.
Yazici et al., "Self-complementary AAV2.5-BMP2-coated femoral allografts mediated superior bone healing versus live autografts in mice with equivalent biomechanics to unfractured femur." *Mol Therapy*, 2001, 19:1416-25.

(Continued)

Primary Examiner — Jane Zara
(74) Attorney, Agent, or Firm — Kilpatrick Townsend & Stockton LLP

(57) ABSTRACT

Provided herein are methods of treating or preventing a bone disorder in a subject.

5 Claims, 6 Drawing Sheets

(56) References Cited

PUBLICATIONS

Zorov et al., "Regulation and Pharmacology of the Mitochondrial Permeability Transition Pore"; Cardiovascular Research, 2009; 83: 213-225.

* cited by examiner

SEQUENCE LISTING

<160> NUMBER OF SEQ ID NOS: 21

<210> SEQ ID NO 1
<211> LENGTH: 207
<212> TYPE: PRT
<213> ORGANISM: Homo sapiens

<400> SEQUENCE: 1

```
Met Leu Ala Leu Arg Cys Gly Ser Arg Trp Leu Gly Leu Leu Ser Val
1               5                   10                  15

Pro Arg Ser Val Pro Leu Arg Leu Pro Ala Ala Arg Ala Cys Ser Lys
            20                  25                  30

Gly Ser Gly Asp Pro Ser Ser Ser Ser Ser Gly Asn Pro Leu Val
        35                  40                  45

Tyr Leu Asp Val Asp Ala Asn Gly Lys Pro Leu Gly Arg Val Val Leu
    50                  55                  60

Glu Leu Lys Ala Asp Val Val Pro Lys Thr Ala Glu Asn Phe Arg Ala
65                  70                  75                  80

Leu Cys Thr Gly Glu Lys Gly Phe Gly Tyr Lys Gly Ser Thr Phe His
                85                  90                  95

Arg Val Ile Pro Ser Phe Met Cys Gln Ala Gly Asp Phe Thr Asn His
            100                 105                 110

Asn Gly Thr Gly Gly Lys Ser Ile Tyr Gly Ser Arg Phe Pro Asp Glu
        115                 120                 125

Asn Phe Thr Leu Lys His Val Gly Pro Gly Val Leu Ser Met Ala Asn
    130                 135                 140

Ala Gly Pro Asn Thr Asn Gly Ser Gln Phe Phe Ile Cys Thr Ile Lys
145                 150                 155                 160

Thr Asp Trp Leu Asp Gly Lys His Val Val Phe Gly His Val Lys Glu
                165                 170                 175

Gly Met Asp Val Val Lys Lys Ile Glu Ser Phe Gly Ser Lys Ser Gly
            180                 185                 190

Arg Thr Ser Lys Lys Ile Val Ile Thr Asp Cys Gly Gln Leu Ser
        195                 200                 205
```

<210> SEQ ID NO 2
<211> LENGTH: 2213
<212> TYPE: DNA
<213> ORGANISM: Homo sapiens

<400> SEQUENCE: 2

```
gcgggactcg gccttctggg cgcgcgcgac gtcagtttga gttctgtgtt ctccccgccc      60
gtgtcccgcc cgacccgcgc ccgcgatgct ggcgctgcgc tgcggctccc gctggctcgg     120
cctgctctcc gtcccgcgct ccgtgccgct gcgcctcccc gcggcccgcg cctgcagcaa     180
gggctccggc gacccgtcct cttcctcctc ctccgggaac ccgctcgtgt acctggacgt     240
ggacgccaac gggaagccgc tcggccgcgt ggtgctggag ctgaaggcag atgtcgtccc     300
aaagacagct gagaacttca gagccctgtg cactggtgag aagggcttcg gctacaaagg     360
ctccaccttc cacagggtga tcccttcctt catgtgccag gcgggcgact tcaccaacca     420
caatggcaca ggcggggaagt ccatctacgg aagccgcttt cctgacgaga actttacact     480
gaagcacgtg gggccaggtg tcctgtccat ggctaatgct ggtcctaaca ccaacggctc     540
ccagttcttc atctgcacca taaagacaga ctggttggat ggcaagcatg ttgtgttcgg     600
tcacgtcaaa gagggcatgg acgtcgtgaa gaaaatagaa tctttcggct ctaagagtgg     660
gaggacatcc aagaagattg tcatcacaga ctgtggccag ttgagctaat ctgtggccag     720
ggtgctggca tggtggcagc tgcaaatgtc catgcaccca ggtggccgcg ttgggctgtc     780
agccaaggtg cctgaaacga tacgtgtgcc cactccactg tcacagtgtg cctgaggaag     840
gctgctaggg atgttagacc tcggccagga cccaccacat tgcttcctaa tacccaccct     900
tcctcacgac ctcatttctg ggcatctttg tggacatgat gtcacccacc ccttgtcaag     960
cattgcctgt gattgcccag cccagattca tctgtgcctt ggacatggtg atggtgatgg    1020
gttgccatcc aagtgaaagt ctttccttg accaagggg acagtcagtt ttgcaaaagg    1080
actctaatac ctgtttaata ttgtcttcct aattgggata atttaattaa caagattgac    1140
tagaagtgaa actgcaacac taacttcccc gtgctgtggt gtgacctgag ttggtgacac    1200
aggccacaga ccccagagct tggcttttga acacaactc agggcttttg tgaaggttcc    1260
cccgctgaga tctttcctcc tggttactgt gaagcctgtt ggtttgctgc gtcgttttt    1320
gaggagggcc catgggggta ggagcagttg aacctgggaa caaacctcac ttgagctgtg    1380
cctagacaat gtgaattcct gtgttgctaa cagaagtggc ctgtaagctc ctgtgctccg    1440
gagggaagca tttcctggta ggctttgatt tttctgtgtg ttaaagaaat tcaatctact    1500
catgatgtgt tatgcataaa acatttctgg aacatggatt tgtgttcacc ttaaatgtga    1560
aaataaatcc tattttctat ggaagactgg tacctggttt ctggaagagg ggtctgtgac    1620
ttggagctga tctttactga gctcgccgtg gcagatgcca tgctcaggac gttcatgtgg    1680
atggtttcat gtcatcgtgc tggcaacttg tcctccctgc cttagagatg aggctcagac    1740
aaacgacctt agcacccata gcctatgcca tgagcactgg ctccaccctg aatcccagct    1800
cctccccctta gtgaccccaa gtctgtttcc ctcagctgca taaggaggcg atatagtttg    1860
aatatttgtc cccagccaaa tctcatgttg aactgtaatc cccagtgctg gaggtggggc    1920
ctgctacgag gtgtttggat catggggacg ggtatttcat ggcttggtgc tgttttcttg    1980
atggtgaatt attgcaagat acggtcattt aaaattgtgt ggcacctccc cctgcccct     2040
tcttgctcct gctttcacca tgtgacatgc ctgatccccc ttcaccttt gccatggtca    2100
taagcttcct gaggcctccc tggaagctga gcagatgcca gcaccatgct tcctgtacat    2160
cctgcagaac cataagccaa ttaaaccttt ttaataataa aaaaaaaaaa aaa           2213

<210> SEQ ID NO 3
<211> LENGTH: 20
<212> TYPE: PRT
```

```
<213> ORGANISM: Artificial sequence
<220> FEATURE:
<223> OTHER INFORMATION: Synthetic construct

<400> SEQUENCE: 3

Glu Phe Gly Gly Val Met Cys Val Glu Ser Val Asn Arg Glu Met Ser
1               5                   10                  15

Pro Leu Val Asp
            20

<210> SEQ ID NO 4
<211> LENGTH: 20
<212> TYPE: PRT
<213> ORGANISM: Artificial sequence
<220> FEATURE:
<223> OTHER INFORMATION: Synthetic construct

<400> SEQUENCE: 4

Arg Glu Met Ser Pro Leu Val Asp Asn Ile Ala Leu Trp Met Thr Glu
1               5                   10                  15

Tyr Leu Asn Arg
            20

<210> SEQ ID NO 5
<211> LENGTH: 20
<212> TYPE: PRT
<213> ORGANISM: Artificial sequence
<220> FEATURE:
<223> OTHER INFORMATION: Synthetic construct

<400> SEQUENCE: 5

Met Cys Val Glu Ser Val Asn Arg Glu Met Ser Pro Leu Val Asp Asn
1               5                   10                  15

Ile Ala Leu Trp
            20

<210> SEQ ID NO 6
<211> LENGTH: 20
<212> TYPE: PRT
<213> ORGANISM: Artificial sequence
<220> FEATURE:
<223> OTHER INFORMATION: Synthetic construct

<400> SEQUENCE: 6

Leu Leu Ser Leu Ala Leu Val Gly Ala Cys Ile Thr Leu Gly Ala Tyr
1               5                   10                  15

Leu Gly His Lys
            20

<210> SEQ ID NO 7
<211> LENGTH: 20
<212> TYPE: DNA
<213> ORGANISM: Artificial sequence
<220> FEATURE:
<223> OTHER INFORMATION: Synthetic construct

<400> SEQUENCE: 7
gtcctcccac tcttagagcc                                            20

<210> SEQ ID NO 8
<211> LENGTH: 20
<212> TYPE: DNA
<213> ORGANISM: Artificial sequence
<220> FEATURE:
<223> OTHER INFORMATION: Synthetic construct
```

<400> SEQUENCE: 8
gtcctcccac tcttagagcc                                           20

<210> SEQ ID NO 9
<211> LENGTH: 20
<212> TYPE: DNA
<213> ORGANISM: Artificial sequence
<220> FEATURE:
<223> OTHER INFORMATION: Synthetic construct

<400> SEQUENCE: 9
cttcccgcct gtgccattgt                                           20

<210> SEQ ID NO 10
<211> LENGTH: 20
<212> TYPE: DNA
<213> ORGANISM: Artificial sequence
<220> FEATURE:
<223> OTHER INFORMATION: Synthetic construct

<400> SEQUENCE: 10
gatgtcctcc cactcttaga                                           20

<210> SEQ ID NO 11
<211> LENGTH: 21
<212> TYPE: DNA
<213> ORGANISM: Artificial sequence
<220> FEATURE:
<223> OTHER INFORMATION: Synthetic construct

<400> SEQUENCE: 11
tgtcctccca ctcttagagc c                                         21

<210> SEQ ID NO 12
<211> LENGTH: 25
<212> TYPE: DNA
<213> ORGANISM: Artificial sequence
<220> FEATURE:
<223> OTHER INFORMATION: Synthetic construct

<400> SEQUENCE: 12
ggaggacauc caagaagauu gucat                                     25

<210> SEQ ID NO 13
<211> LENGTH: 27
<212> TYPE: RNA
<213> ORGANISM: Artificial sequence
<220> FEATURE:
<223> OTHER INFORMATION: Synthetic construct

<400> SEQUENCE: 13
augacaaucu ucuuggaugu ccuccca                                   27

<210> SEQ ID NO 14
<211> LENGTH: 25
<212> TYPE: RNA
<213> ORGANISM: Artificial sequence
<220> FEATURE:
<223> OTHER INFORMATION: Synthetic construct

<400> SEQUENCE: 14
cccaaagaca gcugagaacu ucaga                                     25

<210> SEQ ID NO 15

```
<211> LENGTH: 27
<212> TYPE: RNA
<213> ORGANISM: Artificial sequence
<220> FEATURE:
<223> OTHER INFORMATION: Synthetic construct

<400> SEQUENCE: 15
ucugaaguuc ucagcugucu uugggac                                        27

<210> SEQ ID NO 16
<211> LENGTH: 25
<212> TYPE: RNA
<213> ORGANISM: Artificial sequence
<220> FEATURE:
<223> OTHER INFORMATION: Synthetic construct

<400> SEQUENCE: 16
gcuccaccuu ccacagggug auccc                                          25

<210> SEQ ID NO 17
<211> LENGTH: 27
<212> TYPE: RNA
<213> ORGANISM: Artificial sequence
<220> FEATURE:
<223> OTHER INFORMATION: Synthetic construct

<400> SEQUENCE: 17
gggaucaccc uguggaaggu ggagccu                                        27

<210> SEQ ID NO 18
<211> LENGTH: 25
<212> TYPE: DNA
<213> ORGANISM: Artificial sequence
<220> FEATURE:
<223> OTHER INFORMATION: Synthetic construct

<400> SEQUENCE: 18
cagacugguu ggauggcaag caugt                                          25

<210> SEQ ID NO 19
<211> LENGTH: 27
<212> TYPE: RNA
<213> ORGANISM: Artificial sequence
<220> FEATURE:
<223> OTHER INFORMATION: Synthetic construct

<400> SEQUENCE: 19
acaugcuugc cauccaacca gucuguc                                        27

<210> SEQ ID NO 20
<211> LENGTH: 25
<212> TYPE: RNA
<213> ORGANISM: Artificial sequence
<220> FEATURE:
<223> OTHER INFORMATION: Synthetic construct

<400> SEQUENCE: 20
ggcuaaugcu gguccuaaca ccaac                                          25

<210> SEQ ID NO 21
<211> LENGTH: 27
<212> TYPE: RNA
<213> ORGANISM: Artificial sequence
<220> FEATURE:
<223> OTHER INFORMATION: Synthetic construct
```

```
<400> SEQUENCE: 21
guugguguua ggaccagcau uagccau                                              27
```

USE OF CYCLOPHILIN D INHIBITORS TO TREAT OR PREVENT BONE DISORDERS

CROSS REFERENCE TO RELATED APPLICATIONS

This application claims the benefit of U.S. Provisional Application No. 61/736,072, filed on Dec. 12, 2012, which is incorporated by reference herein in its entirety.

FEDERALLY SPONSORED RESEARCH OR DEVELOPMENT

This invention was made with government support under Grant Nos. AR061515, AR061307 and AR064610 awarded by the National Institutes of Health. The government has certain rights in the invention.

BACKGROUND

Bone disorders and fractures result in hospitalizations and a notable economic burden on health care systems. For example, osteoporosis, found in the majority of the elderly population, leads to increased risk of fracture and delayed fracture healing. Moreover, the number of bone fractures caused by an age-related disease, such as osteoporosis, may escalate in industrial nations in the coming years with increasing life expectancy. Therefore, new therapies for bone disorders are necessary.

SUMMARY

Provided herein are methods of treating or preventing a bone disorder in a subject. The methods comprise administering to a subject with or at risk of developing a bone disorder an effective amount of a cyclophilin D inhibitor.

Further provided is a method of accelerating bone healing in a subject suffering from a bone fracture comprising administering to a subject in need of bone healing an effective amount of a cyclophilin D inhibitor.

Also provided is a method of promoting osteogenesis in a subject with decreased osteogenesis, comprising administering to a subject with decreased osteogenesis an effective amount of a cyclophilin D inhibitor. The subject can have decreased osteogenesis as compared to a control.

Further provided is a method of treating or preventing a bone disorder in a subject, comprising administering to a subject with or at risk of developing a bone disorder an effective amount of mesenchymal stem cells (MSCs), wherein the cells are modified to reduce expression of CypD as compared to unmodified cell

DETAILED DESCRIPTION

Figure 1:
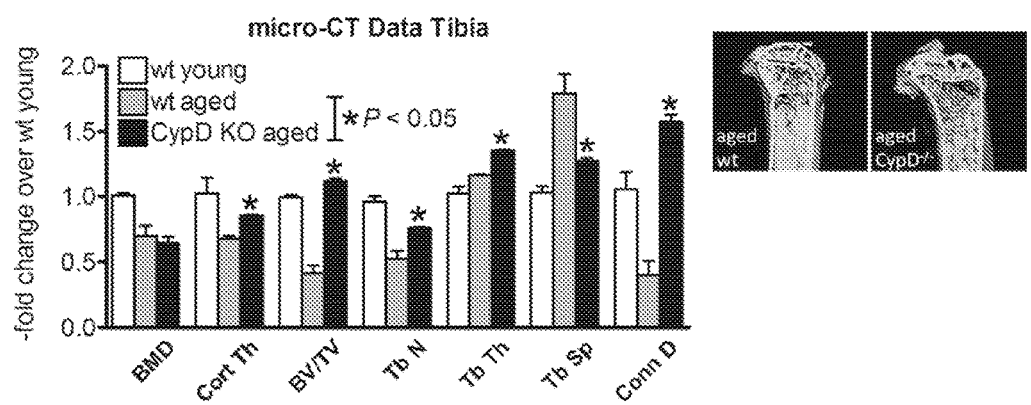
FIG. 1 shows that cyclophilin D knockout improves bone quality, as evidenced by micro-CT analysis of tibia from young and aged wild-type (wt) and aged CypD knock-out (KO) mice. * indicates P<0.05 (aged CypD KO vs wt), n=3. Insert shows tibial trabecular bone in aged wt or CypD KO mice.

Provided herein is a method of treating or preventing a bone disorder in a subject, comprising administering to a subject with or at risk of developing a bone disorder an effective amount of a cyclophilin D inhibitor.

Throughout this application, by treating is meant a method of reducing or delaying one or more effects or symptoms of a disease. Treatment can also refer to a method of reducing the underlying pathology rather than just the symptoms. The treatment can be any reduction and can be, but is not limited to, the complete ablation of the disease or the symptoms of the disease. Treatment can include the complete amelioration of a disease as detected by art-known techniques. Art recognized methods are available to detect bone disorders and their symptoms. These include, but are not limited to, ultrasonometric evaluation, bone density scan, radiological examination, histological examination, MRI, musculoskeletal evaluation or combinations of these methods. For example, a disclosed method is considered to be a treatment if there is about a 10% reduction in one or more symptoms of the disease in a subject when compared to the subject prior to treatment or control subjects. Thus, the reduction can be about a 10, 20, 30, 40, 50, 60, 70, 80, 90, 100%, or any amount of reduction in between.

As utilized herein, by prevent, preventing, or prevention is meant a method of precluding, delaying, averting, obviating, forestalling, stopping, or hindering the onset, incidence, severity, or recurrence of a disease, for example, a bone disorder. For example, the disclosed method is considered to be a prevention if there is a reduction or delay in onset, incidence, severity, or recurrence of osteoporosis or one or more symptoms of osteoporosis (e.g., pain, loss of height, fracture) in a subject susceptible to osteoporosis as compared to control subjects susceptible to osteoporosis that did not receive a cyclophilin D inhibitor. The disclosed method is also considered to be a prevention if there is a reduction or delay in onset, incidence, severity, or recurrence of osteoporosis or one or more symptoms of osteoporosis in a subject susceptible to osteoporosis after receiving a cyclophilin D inhibitor as compared to the subject's progression prior to receiving treatment. Thus, the reduction or delay in onset, incidence, severity, or recurrence of osteoporosis can be about a 10, 20, 30, 40, 50, 60, 70, 80, 90, 100%, or any amount of reduction in between. The examples set forth above for osteoporosis are merely exemplary as these examples are applicable to any bone disorder set forth herein.

As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

As utilized herein, bone disorders include, but are not limited to, osteoporosis, osteopenia, osteomalacia, osteodystrophy, osteoarthritis, osteomyeloma, arthritis, bone fracture, Paget's disease, osteogenesis imperfecta, bone sclerosis, aplastic bone disorder, humoral hypercalcemic myeloma, multiple myeloma, bone thinning following metastasis and hypercalcemia.

Cyclophilin D (CypD) is a member of the peptidyl-prolyl cis-trans isomerase (PPIase) family. PPIases catalyze the cis-trans isomerization of proline imidic peptide bonds in oligopeptides and accelerate the folding of proteins. This protein is part of the mitochondrial permeability transition pore in the inner mitochondrial membrane. Although the methods described herein are not limited to humans, GenBank Accession No. NP_005720.1 (SEQ ID NO: 1) provides a protein sequence for human cyclophilin D that is encoded by the nucleotide sequence set forth under GenBank Accession No. NM_005729.3 (SEQ ID NO: 2). Amino acids 1-29 of SEQ ID NO: 1 encode a signal peptide. The mature peptide is encoded by amino acids 30-207 of SEQ ID NO: 1. The information, including the sequences, provided under GenBank Accession No. NP_005720.1 and GenBank Accession No. NM_005729.3, is herein incorporated in its entirety by this reference.

The CypD sequences contemplated herein include full-length wild-type sequences, as well as allelic variants or homologs that retain at least one CypD activity, for example, PPIase activity. For example, the sequences set forth herein can comprise one or more amino acid substitutions. CypD sequences from other species are also available to those of skill in the art. CypD sequences also include sequences that are at least 50%, 60%, 70%, 80%, 90%, 95%, 98%, 99% or 100% identical to a CypD sequence set forth herein that still retains at least one activity of CypD, for example, PPIase activity.

Those of skill in the art readily understand how to determine the identity of two polypeptides or nucleic acids. For example, the identity can be calculated after aligning the two sequences so that the identity is at its highest level.

Another way of calculating identity can be performed by published algorithms. Optimal alignment of sequences for comparison can be conducted using the algorithm of Smith and Waterman *Adv. Appl. Math.* 2: 482 (1981), by the alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information (http://www.ncbi.nlm.nih.gov/blast/b12seq/b12.html), or by inspection.

The same types of identity can be obtained for nucleic acids by, for example, the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 that are herein incorporated by this reference for at least material related to nucleic acid alignment. It is understood that any of the methods typically can be used and that, in certain instances, the results of these various methods may differ, but the skilled artisan understands if identity is found with at least one of these methods, the sequences would be said to have the stated identity.

For example, as used herein, a sequence recited as having a particular percent identity to another sequence refers to sequences that have the recited identity as calculated by any one or more of the calculation methods described above. For example, a first sequence has 80 percent identity, as defined herein, to a second sequence if the first sequence is calculated to have 80 percent identity to the second sequence using the Zuker calculation method even if the first sequence does not have 80 percent identity to the second sequence as calculated by any of the other calculation methods. As yet another example, a first sequence has 80 percent identity, as defined herein, to a second sequence if the first sequence is calculated to have 80 percent identity to the second sequence using each of the calculation methods (although, in practice, the different calculation methods will often result in different calculated identity percentages).

As shown in the Examples, inhibition of cyclophilin D function leads to restoration of MSC osteogenicity and mitochondrial function, and to improved bone quality during aging. Therefore, inhibition of cyclophilin D is useful for treating or preventing a bone disorder in a subject. In the methods set forth herein, cyclophilin D can be inhibited by decreasing the activity of cyclophilin D, decreasing the amount of cyclophilin D mRNA, or decreasing the expression of cyclophilin D protein, to name a few. Cyclophilin D can also be inhibited by knocking down or knocking out cyclophilin D in cells. These cells can be in vitro, ex vivo or in vivo. Inhibition of cyclophilin D function does not have to be complete as this can range from a slight reduction to complete reduction of cyclophilin D function. For example, a reduction can be about a 10, 20, 30, 40, 50, 60, 70, 80, 90 or 100% reduction. Percentage reductions in between these values are also contemplated Inhibitors of cyclophilin D include, but are not limited to, a chemical, a small or large molecule (organic or inorganic), a drug, a peptide, a cDNA, an antibody, an aptamer, a morpholino, a triple helix molecule, an siRNA, a shRNA, an miRNA, an antisense RNA, a ribozyme or any other compound now known or identified in the future that inhibits at least one function of cyclophilin D, for example, PPIase activity.

Examples of cyclophilin D inhibitors include, but are not limited to, N-methyl-4-isoleucine cyclosporin (NIM811), Debio 025 (alisporivir), Sanglifehrin A, cyclosporin A and GW5. Quinoxaline derivatives can also be used. See, for example, Guo et al. *Acta Pharmacologica Sinica* 10: 1201-1211 (2005)). The structures for N-methyl-4-isoleucine cyclosporin (NIM811), Debio 025 (alisporivir), Sanglifehrin A, cyclosporin A and GW5 are set forth below.

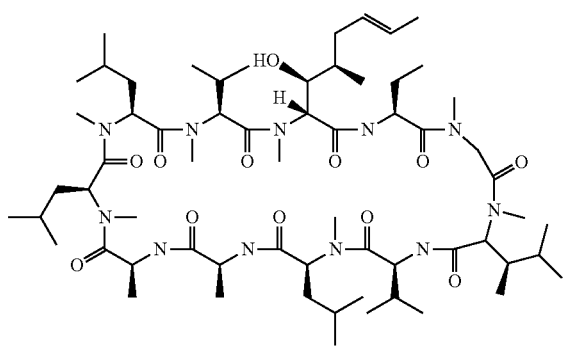

NIM811

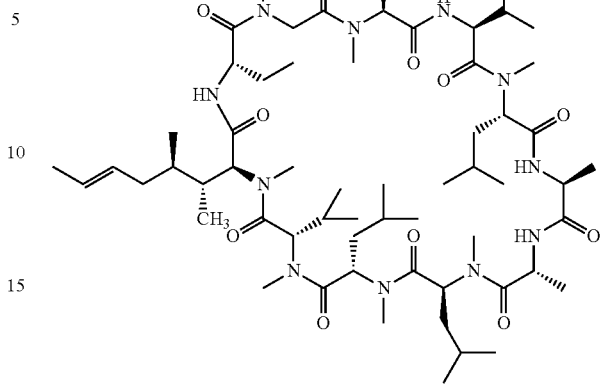

Cyclosporin A

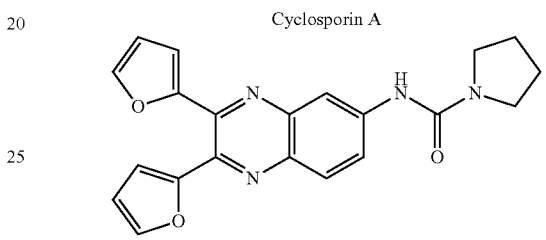

GW5

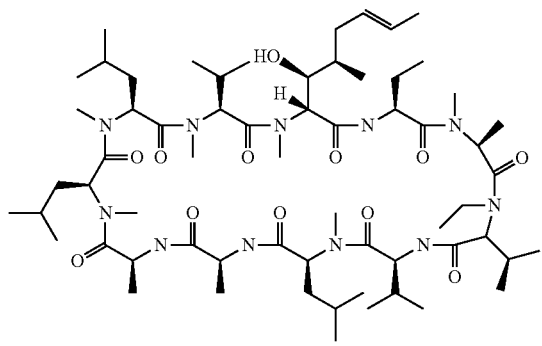

Debio 025 (alisporivir)

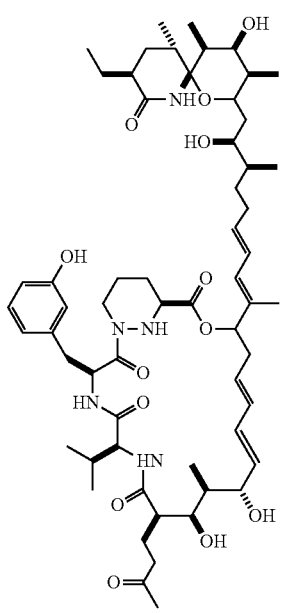

Sanglifehrin A

Derivatives and pharmaceutically acceptable salts of all of the compounds set forth herein are also provided. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein.)

Other inhibitors include peptides such as, for example, EFGGVMCVESVNREMSPLVD (SEQ ID NO: 3), REMSPLVDNIALWMTEYLNR (SEQ ID NO: 4), MCVESVNREMSPLVDNIALW (SEQ ID NO: 5) and LLSLALVGAC- ITLGAYLGHK (SEQ ID NO. 6). These and other peptides can be fused to carriers, for example, via peptide linkers. These linkers can range in size from about 2 amino acid residues to about 20 amino acid residues. The carriers can be, but are not limited to, a liposome, a nanoparticle, a cell penetrating peptide or a micelle. The peptide can also be linked to another peptide that targets a cell surface receptor in order to effect targeting of the peptide inhibitor to particular cell types. For example, the peptide can be linked to a ligand that binds to a cell surface receptor or an antibody that recognizes a cell surface protein.

Antisense molecules can also be used. For example, 5'GTCCTCCCACTCTTAGAGCC-3' (SEQ ID NO: 7), 5'-GTCCTCCCACTCTTAGAGCC-3' (SEQ ID NO: 8), 5'-CTTCCCGCCTGTGCCATTGT-3' (SEQ ID NO: 9), 5'-GATGTCCTCCCACTCTTAGA-3' (SEQ ID NO: 10), and 5'-TGTCCTCCCACTCTTAGAGCC-3' (SEQ ID NO: 11) are examples of antisense molecules that can be used to inhibit cyclophilin D.

Examples of siRNa molecules that can be used to inhibit cyclophilin D include but are not limited to:

```
                                          (SEQ ID NO: 12)
5'-rGrGrArGrGrArCrArUrCrCrArArGrArArGrArUrUrGrUr
CAT-3'

(SEQ ID NO: 13)
5'-rArUrGrArCrArArUrCrUrUrCrUrGrGrArUrGrUrCrCr
UrCrCrA-3'

(SEQ ID NO: 14)
5'-rCrCrArArArGrArCrArGrCrUrGrArGrArArCrUrUrCr
AGA-3'

(SEQ ID NO: 15)
5'-rUrCrUrGrArArGrUrUrCrUrCrArGrCrUrGrUrCrUrUrUr
GrGrGrArC-3'

(SEQ ID NO: 16)
5'-rGrCrUrCrCrArCrCrUrUrCrCrArCrArGrGrGrUrGrArUr
CCC-3'

(SEQ ID NO: 17)
5'-rGrGrGrArUrCrArCrCrCrUrGrUrGrGrArArGrGrUrGrGr
ArGrCrCrU-3'

(SEQ ID NO: 18)
5'-rCrArGrArCrUrGrGrUrUrGrGrArUrGrGrCrArArGrCrAr
UGT-3'

(SEQ ID NO: 19)
5'-rArCrArUrGrCrUrUrGrCrCrArUrCrCrArArCrCrArGrUr
CrUrGrUrC-3'

(SEQ ID NO: 20)
5'-rGrGrCrUrArArUrGrCrUrGrGrUrCrCrUrArArCrArCrCr
AAC-3'

(SEQ ID NO: 21)
5'-rGrUrUrGrGrUrGrUrArGrGrArCrCrArGrCrArUrUrAr
GrCrCrArU-3'
```

In the methods set forth herein, one or more cyclophilin D inhibitors can be administered in combination or concomitantly with other therapeutic compounds such as, for example, bisphosphonate (nitrogen-containing and non-nitrogen-containing), testosterone, estrogen, sodium fluoride, strontium ranelate, vitamin D and its analogs, an antibiotic, an immunosuppressant, calcitonin, calcium supplements, selective estrogen receptor modulators (SERMs, e.g., raloxifene), osteogenic proteins (e.g., BMP2, BMP-4, BMP-5, BMP-6, BMP-7, BMP-9, BMP-10, BMP-12, BMP-13, MP52, or heterodimers thereof), statins, activators of Estrogen-Like Signaling (ANGELS), and parathyroid hormone (PTH).

Any of the methods set forth herein, can further comprise administering an anti-inflammatory agent to the subject. Examples of anti-inflammatory agents include, but are not limited ImSAIDs, NSAIDS and steroids.

In any of the methods provided herein, administration of a cyclophilin D inhibitor can increase osteogenicity of mesenchymal stem cells in the subject and/or increase mitochondrial function in the subject. An increase in osteogenicity in mesenchymal cells can be an increase in osteogenic differentiation of MSCs that is effected by increased mitochondrial function. An increase in osteogenicity of mesenchymal cells can be measured by isolating MSCs from bone marrow and measuring the expression of osteogenic markers such as alkaline phosphatase and Runx2, for example, by using real-time RT-PCR. Increases can be, for example, percentage increases of about 10, 20, 30, 40, 50, 60, 70, 80, 90, 100, 200, 300, 400% or greater.

Further provided is a method of accelerating bone healing in a subject suffering from a bone fracture comprising administering to a subject in need of bone healing an effective amount of a cyclophilin D inhibitor. The bone fracture can be selected from the group consisting of a traumatic fracture, a fatigue fracture, a pathologic fracture or a surgical fracture. A traumatic fracture is a fracture caused by a traumatic event, for example, an accident, a fall, a gunshot wound etc., as opposed to genetic or natural causes. A fatigue fracture can occur as a result of repeated or unusual endogenous stress. A pathologic fracture can be, but is not limited to, a fracture associated with a disease selected from the group consisting of osteoporosis, arthritis, osteoarthritis and Paget's disease. Thus, a bone fracture can result as a consequence of a bone disorder. As used throughout, a surgical fracture of a bone is a controlled cut created in a bone in order to re-align a structural deformity or to create mechanical stability from a weakened part.

Acceleration of bone healing can be a reduction or a decrease in the amount of time it takes for a bone to heal as compared to control subjects that did not receive a cyclophilin D inhibitor. This can also be a reduction or a decrease in the amount of time it takes for a bone to heal as compared to the subject's progression prior to receiving cyclophilin D. The reduction can be any reduction and can be, about a 10, 20, 30, 40, 50, 60, 70, 80, 90, 95, 96, 97, 98 or 99% reduction in the time it takes for a bone to heal. Art recognized methods are available to measure bone healing. These include, but are not limited to, ultrasonometric evaluation, bone density scan, radiological examination, histological examination, MRI and musculoskeletal evaluation. Acceleration of bone healing can occur at any stage of bone healing. For example, acceleration of bone healing can be an acceleration in haematoma formation. This is also known as the inflammation or granulation phase. During this phase, activated platelets release a variety of products, including fibronection, platelet derived growth factor and transforming growth factor beta, which trigger the influx of inflammatory cells. The subsequent cytokine cascade brings the cells of repair (fibroblasts, endothelial cells and osteoblasts) into the fracture gap. Acceleration of bone healing can also be an acceleration of soft callus formation characterized by the formation of connective tissues, including cartilage and formation of new capillaries from pre-existing vessels. This is also known as the proliferative phase. Acceleration of bone healing can also be an acceleration of hard callus formation. This phase is also known as the maturing or modeling phase. This phase is characterized by the formation of woven bone, either directly from mesenchymal tissue (intramembranous) or via an intermediate stage of cartilage (endochondral or chondroid routes). Acceleration of bone healing can also be an acceleration of the remodeling phase where woven bone is remodelled into stronger lamellar bone by the orchestrated action of osteoclast bone resorption and osteoblast bone formation.

Also provided is a method of promoting osteogenesis in a subject with decreased osteogenesis, comprising administering to a subject with decreased osteogenesis as compared to a control an effective amount of a cyclophilin D inhibitor. This method can further comprise diagnosing the subject with decreased osteogenesis prior to administration of a cyclophilin D inhibitor.

As used throughout, osteogenesis is the process of bone tissue formation or laying down of new bone material by osteoblasts. Osteoblasts are mononucleate cells that are responsible for bone formation. The number of osteoblasts tends to decrease with age, affecting the balance of formation and resorption in bone tissue. Decreased bone formation or osteogenesis in aging can be due to decreased osteogenic potential of mesenchymal stem cells (MSCs), precursors of bone-forming osteoblasts. Thus, a subject with decreased osteogenesis can be a subject that has a reduced number of osteoblasts or a subject whose MSCs have decreased osteogenic potential as compared to a control subject.

A subject with decreased osteogenesis can be a subject with a bone disorder, for example, osteoporosis, osteopenia, osteomalacia, osteodystrophy, osteoarthritis, osteomyeloma, arthritis, bone fracture, Paget's disease, osteogenesis imperfecta, bone sclerosis, aplastic bone disorder, humoral hypercalcemic myeloma, bone thinning following metastasis or hypercalcemia. A subject with decreased osteogenesis can also be subject with bone fracture. Therefore, a control subject can be a healthy subject that does not have a bone disorder or a bone fracture. A control subject can also be a subject who has or is undergoing therapy to promote osteogenesis, wherein the therapy is not administration of a cyclophilin D inhibitor.

As used throughout, promoting osteogenesis means to increase the amount of osteoblasts and/or the amount of bone tissue formation in the subject. This increase can be a 10, 20, 30, 40, 50, 60, 70, 80, 90, 100, 200, 300, 400% or greater. The percentage increase can also be any percentage in between these amounts. The number of osteoblasts and/or the amount of bone formation can be measured by taking bone biopsies from the iliac crest before and after treatment. Prior to biopsy, subjects receive two courses of mineral apposition label allowing detection of the mineral apposition rate in a biopsy specimen. Quantitative bone histomorphometry is then performed. Osteoblasts are identified as flattened or cuboidal cells that line the osteoid surface (See, for example, H. E. Gruber, J. Grigsby, C. H. Chesnut, *Calcif Tissue Int* (2000) 66:29-34).

Further provided is a method of treating or preventing a bone disorder in a subject, comprising administering to a subject with or at risk of developing a bone disorder an effective amount of mesenchymal stem cells (MSCs), wherein the MSCs are modified to reduce expression of CypD as compared to an unmodified cell(s). The unmodified cells can be unmodified MSC cells. The cells can be administered to the subject using numerous administration methods described herein. For example, the cells can be administered systemically. The cells can also be injected into a bone or a fracture site. The cells can also be transplanted into a subject in or as part of a bone graft. As described in the Examples, the cells can be from the same subject (for example, for autologous MSC therapy) or from a different subject (for example, for allogeneic MSC therapy). One of skill in the art would know how many cells to administer depending on the mode of administration, the type of bone disorder and other parameters associated with treating or preventing a bone disorder.

The cells obtained from a subject can be modified ex vivo to reduce CypD expression. The reduction in CypD expression can be about 10, 20, 30, 40, 50, 60, 70, 80, 90, 100%, or any amount in between. Methods for reducing or knocking down CypD expression are known in the art. For example, the cells can be modified by contacting the cells with an siRNA, shRNA, an antisense or miRNA that targets CypD, in order to reduce CypD expression. A vector that knocks out the CypD gene entirely can also be used to modify the cells. The present disclosure includes all forms of nucleic acid delivery including synthetic oligos, naked DNA, plasmid and viral delivery, whether integrated into the genome of the cells or not. Also provided are pharmaceutical compositions comprising the modified MSCs described herein.

The agents described herein can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012)

Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and *acacia*, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butylenegly-col, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents. Administration can be carried out using therapeutically effective amounts of the agents described herein for periods of time effective to treat a bone disorder, accelerate bone healing and/or increasing osteogenicity. The effective amount can be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent can be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

Any appropriate route of administration can be employed, for example, parenteral, intravenous, subcutaneous, intramuscular, intraventricular, intracorporeal, intraperitoneal, rectal, or oral administration. Administration can be systemic or local. Pharmaceutical compositions can be delivered locally to the area in need of treatment, for example by topical application or local injection. Any of the compositions can be delivered via an implant that releases a bone healing composition. For example, a microchip that is programmed to release one or more compositions can be implanted in the subject to deliver the composition to the bones of the subject and/or the site of a fracture. Multiple administrations and/or dosages can also be used. Effective doses for any of the administration methods described herein can be extrapolated from dose-response curves derived from in vitro or animal model test systems.

Bone cements can also be used to deliver any of the compositions described herein. Bone cements have pores from which a composition provided herein diffuses. The rate of diffusion of the composition from the bone cement can depend on the pore size of the cement used and the properties of the composition used. The amount of composition infiltrated per unit volume of bone cement or per weight of bone cementing agent or of cementing agent component can therefore be adjusted based on, for example, the particular cyclophilin D inhibitor used, the particular cement used, and the like. It can also be adjusted depending, for example, on clinical factors such as, but not limited to, the type of bone disorder, fracture etc., and the location and type of procedure. PMMA or PM (both abbreviations for polymethylmethacrylate) bone cements are effective cements for delivery of the compositions provided herein.

Some bone cementing agent components or bone cements that comprise cementing agents that can be infiltrated with, for example, a cyclophilin D inhibitor include, but are not limited to, those from Stryker (Kalamazoo, Mich.), Zimmer (Warsaw, Ind.), DePuy (Warsaw, Ind.), Biomet (Warsaw, Ind.), and Smith & Nephew (Memphis, Tenn.). For example, a cyclophilin D inhibitor can be mixed under sterile conditions with individual batches of Depuy (Wardaw, Ind.) Smartset HVC® Polymethymethacrylated bone cement or bone cement cementing agent component. The cementing agent component can comprise a cementing agent such as polymethylmethacrylate and/or methylmethacrylate. The cementing agent component can be infiltrated with one or more cyclophilin D inhibitors. Optionally, the bone cement can comprise one or more antimicrobial agents such as, for example, an antibacterial agent. Antibacterial agents include, but are not limited to silver, erythromycin, clindamycin, vancomycin and gentamicin.

Additionally, the bone cement can comprise radiopaque compositions or compositions for providing desired setting and handling characteristics. For example, the bone cement can comprise methyl-methacrylate-styrene copolymer, polymethylmethacrylate, barium sulfate, benzoyl peroxide, methylmethacrylatemethylacrylate copolymer, methylmethacrylate homopolymer, zirconium dioxide, and chlorophyll. Such compositions can be mixed with the cementing agent component for combination with a liquid component. The liquid component for mixing with the powder component can be a liquid monomer. Optionally, the liquid component can be mixed with a bone cementing agent component comprising the cementing agent and the cyclophilin D inhibitor to form a bone cement. Optionally, the liquid component comprises methylmethacrylate and N,N-dimethyl-p-toluidine. Also provided are compositions comprising polymethylmethacrylate or methylmethacrylate infiltrated with a composition described herein.

The disclosure also provides a pharmaceutical pack or kit comprising one or more containers filled with one or more of the ingredients of the pharmaceutical compositions. Instructions for use of the composition can also be included.

In an example in which a nucleic acid is employed, such as an antisense or an siRNA molecule, the nucleic acid can be delivered intracellularly (for example by expression from a nucleic acid vector or by receptor-mediated mechanisms), or by an appropriate nucleic acid expression vector which is administered so that it becomes intracellular, for example by use of a retroviral vector (see U.S. Pat. No. 4,980,286), or by direct injection, or by use of microparticle bombardment (such as a gene gun; Biolistic, Dupont), or coating with lipids or cell-surface receptors or transfecting agents, or by administering it in linkage to a homeobox-like peptide which is known to enter the nucleus (for example Joliot et al., *Proc. Natl. Acad. Sci. USA* 1991, 88:1864-8). siRNA carriers also include, polyethylene glycol (PEG), PEG-liposomes, branched carriers composed of histidine and lysine (HK polymers), chitosan-thiamine pyrophosphate carriers, surfactants (for example, Survanta and Infasurf), nanochitosan carriers, and D5W solution. The present disclosure includes all forms of nucleic acid delivery, including synthetic oligos, naked DNA, plasmid and viral delivery, whether integrated into the genome or not.

Physical transduction techniques can also be used, such as liposome delivery and receptor-mediated and other endocytosis mechanisms (see, for example, Schwartzenberger et al., *Blood* 87:472-478, 1996) to name a few examples. These methods can be used in conjunction with any of these or other commonly used gene transfer methods.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications can be made. Accordingly, other embodiments are within the scope of the following claims.

EXAMPLES

Decreased bone formation in aging is partly due to decreased osteogenic potential of mesenchymal stem cells (MSCs), precursors of bone-forming osteoblasts. Activation of mitochondria is required for osteogenic differentiation of MSCs. Studies described herein show that the mitochondrial permeability transition (MPT) pore, a non-selective mitochondrial pore plays a major role in osteogenic differentiation. Also shown herein is that a mitochondrial protein, cyclophilin D (CypD), is a major regulator of the MPT.

CypD Knock-Out Mice

CypD knock-out mice are an effective model of MPT loss-of-function. CypD (PPIF) knock-out mice (strain B6;129-Ppif$^{tm1Lmol}$/J) were obtained from the Jackson Laboratory (Bar Harbor, Me.).

Bone quality, MSC bioenergetic and MSC osteogenic functions in aged CypD knock-out mice in comparison to aged wild-type mice were studied. These studies showed that bone quality in aged CypD knock-out mice is significantly higher than the bone quality in aged wild-type (wt) mice. This is evident from the micro-CT studies, shown in FIG. 1, which demonstrate a significant loss of bone in aged wt mice, such as the decrease in bone mineral density (BMD), cortical thickness (Cort Th), bone to total volume (BV/TV), trabecular number (Tb N), connectivity density (Conn D) and an increase in trabecular space (Tb Sp).

Knockout mice were examined as follows. The mice were allowed to age until 13 months of age. Micro-CT (computerized tomography) analysis of femoral, tibial and vertebral bone was performed in wt young (3 month), wt aged (13 month) and CypD KO aged (13 month) mice. This method allows accurate quantitative assessment of bone quality parameters listed above. All three groups were compared and statistical analysis was performed. Bone samples were also taken for histology analysis. Tissue samples were fixed, decalcified, sectioned and analyzed using quantitative bone histomorphometry.

Inhibition of CypD Leads to Improved Bone Quality in Aged Mice

As described above, aged CypD knock-out (KO) mice have significantly better bones than their wt counterparts, as evident from higher Cort Th, BV/TV, Tb N, Tb Th and Conn D values, and a significantly lower Tb Sp value. Histology confirmed the micro-CT data.

Inhibition of CypD Leads to Improved Osteogenic Potential in Aged Mice

Figure 2A:
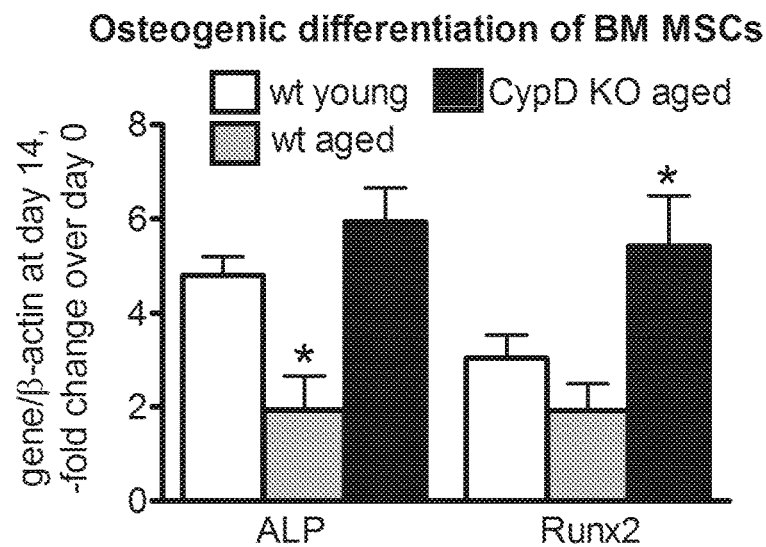
FIG. 2A shows that cyclophilin D knockout improves mesenchymal stem cell (MSC) osteogenic function in aged mice. Bone marrow (BM) MSCs were isolated from young and aged wt and aged CypD KO mice and incubated in osteogenic media for 14 days. ALP and Runx2 gene expression was assessed. * indicates P<0.05 vs Day 0, n=2.

MSCs isolated from bone marrow were incubated in osteogenic media with ascorbate and b-glycerophosphate for 7, 10, 14 and 21 days. Osteogenic differentiation was confirmed with Alizarin Red staining and by measuring expression of alkaline phosphatase (ALP) and Runx2 using standard real-time RT-PCR techniques. As shown in FIG. 2A, MSCs isolated from bone marrow of aged CypD knock-out mice show improved osteogenic potential, indicated by significantly higher expression of osteogenic markers, alkaline phosphatase (ALP) and Runx2, when compared to the aged wild-type mice and similarly to the young wild-type mice.

Figure 2B:
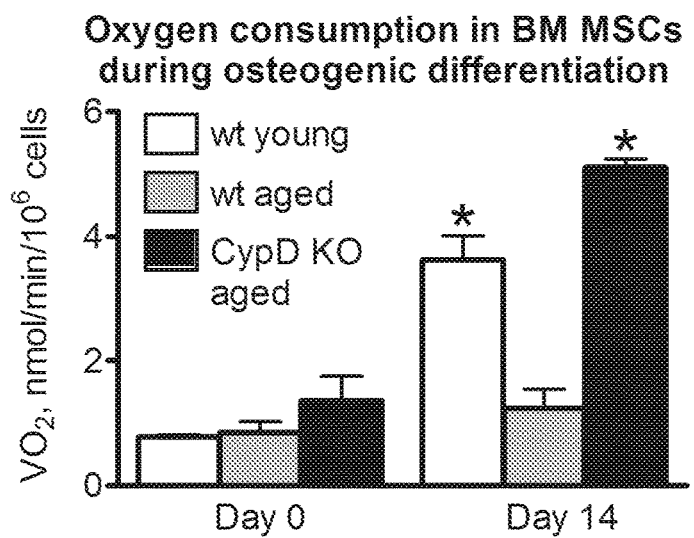
FIG. 2B shows that cyclophilin D knockout improves mesenchymal stem cell bioenergetic functions in aged mice. Bone marrow (BM) MSCs were isolated from young and aged wt and aged CypD KO mice and incubated in osteogenic media for 14 days. Cell respiration was assessed. * indicates P<0.05 vs Day 0, n=2.

Mitochondrial function was assessed by measuring oxygen consumption rate (VO$_2$) by cells using a Clark type oxygen electrode in a sealed chamber as described in Shapovalov et al. (*J Biol Chem.* 286, 22331-8 (2011)). Higher VO$_2$ indicates improved mitochondrial function. Improved mitochondrial function was seen in MSCs isolated from bone marrow of aged CypD knock-out mice, as shown by increased cell respiration when compared to the aged wild-type mice and similarly to the young wild-type mice (FIG. 2B). Together, these data indicate that the loss of function of CypD leads to restoration of MSC osteogenicity and mitochondrial function and to improved bone quality during aging. This is the first time that this mechanism, i.e., MPT regulation via CypD, has been identified as affecting bioenergetics, osteogenicity and viability in aged MSC. Thus, inhibition of CypD is a viable therapy for increasing osteogenicity and treating bone disorders.

Inhibition of CypD Leads to Improved Bone Structure in Aged Mice

Figure 3:
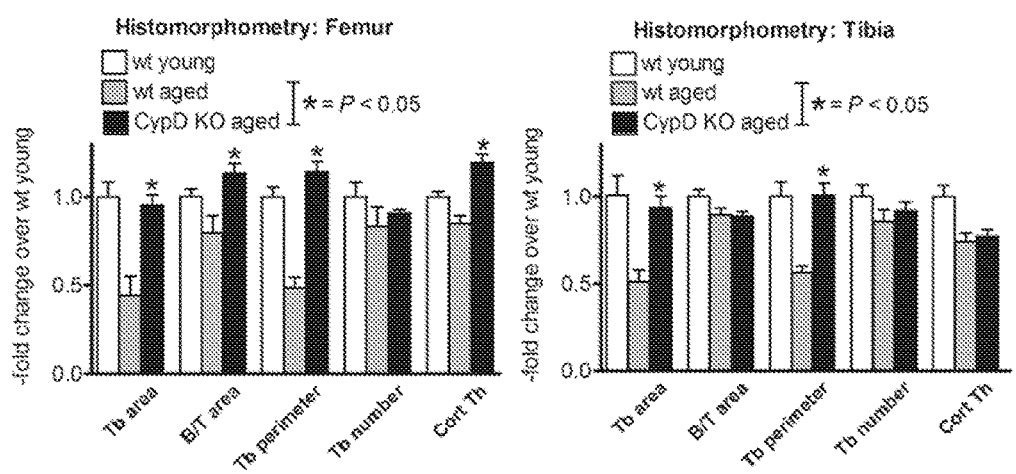
FIG. 3 shows significant increases of trabecular (Tb) area and Tb perimeter in both femur and tibia of aged CypD KO mice when compared to aged wt mice. Data are mean+/−S.E., n=5 (B/T—bone to total, Cort Th—cortical thickness).

It was also shown that inhibition of CypD leads to improved bone structure in aged mice. In addition to micro-CT analysis, histology data was collected and histomorphometry analysis of the effect of CypD knock-out (KO) on mouse bone structure was performed using OsteoMeasur™ software. Sections of decalcified bone stained with hematoxylin and eosin were visualized and analyzed using the Osteomeasure™ system in semi-automatic mode. Similar regions of long bones below the growth plate were chosen for analysis; cortical and trabecular bone was traced; and the following parameters derived: trabecular (Tb) area, B/T area (trabecular bone area relative to the total bone marrow area), trabecular (Tb) perimeter, trabecular (Tb) number, and cortical thickness (Cort Th). FIG. 3 shows significant increases of trabecular (Tb) area and Tb perimeter in both femur and tibia of aged CypD KO mice when compared to the aged wt mice. Data are mean+/−S.E., n=5 (B/T—bone to total, Cort Th—cortical thickness).

Inhibition of CypD Leads to Improved Bone Strength in Aged Mice

Inhibition of CypD also leads to improved bone strength in aged mice. Biomechanical testing of femoral bones from young wt, aged wt and aged CypD KO mice was performed via a commonly used torsion testing method at 1°/s until failure using an EnduraTec TestBench system. Torsional testing was performed as described in Yazici et al., (*Mol Therapy,* 19, 1416-25 (2011)).

Figure 4:
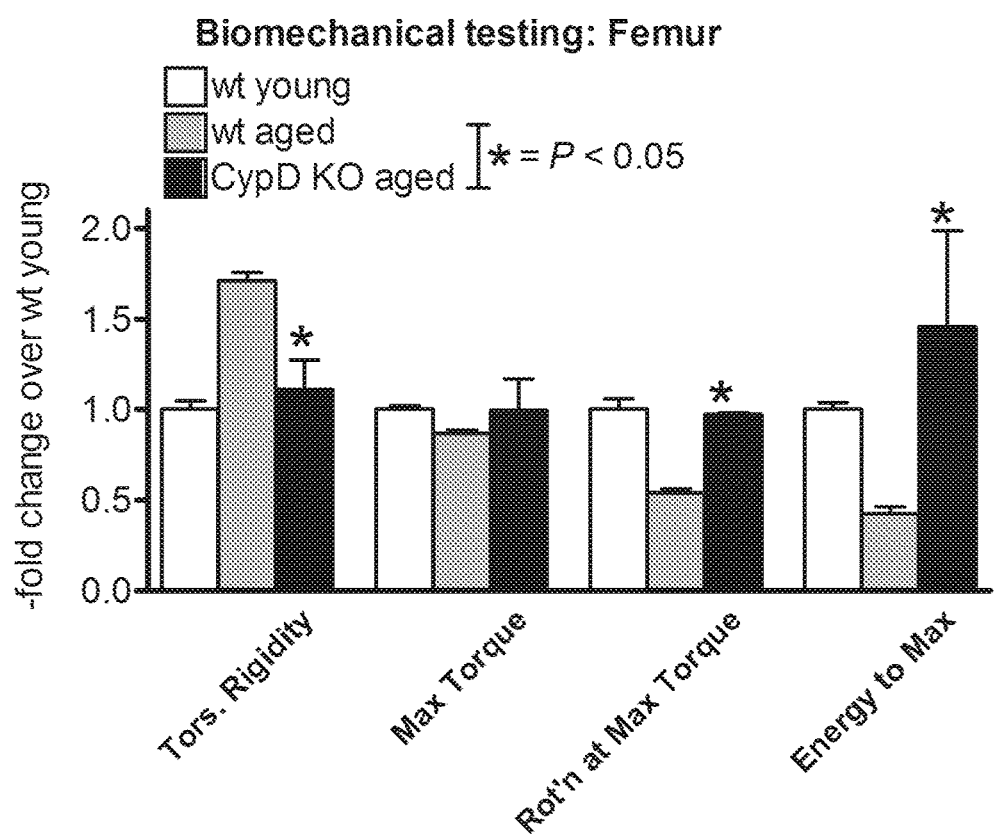
FIG. 4 shows that inhibition of CypD leads to improved bone strength in aged mice. Most of the values indicate significant changes in aged wt mice indicating more rigid (increased Tors rigidity) and fragile (decreased Rot'n at Max and Energy to Max) bone. These parameters were restored to wt young values in aged CypD KO mice, indicating less rigid and stronger bones. Data are mean+/−S.E., n=3.

The following biomechanical values were determined: torsional (Tors) rigidity, maximum (Max) torque, rotation (Rot'n) at maximum torque, and energy to maximum (Max). As shown in FIG. 4, most of these values indicate significant changes in aged wt mice indicating more rigid (increased Tors rigidity) and fragile (decreased Rot'n at Max and Energy to Max) bone. These parameters were restored to wt young values in aged CypD KO mice, indicating less rigid and stronger bones. Data are mean+/−S.E., n=3.

Inhibition of CypD Leads to Accelerated Bone Fracture Healing in Aged Mice

Figure 5:
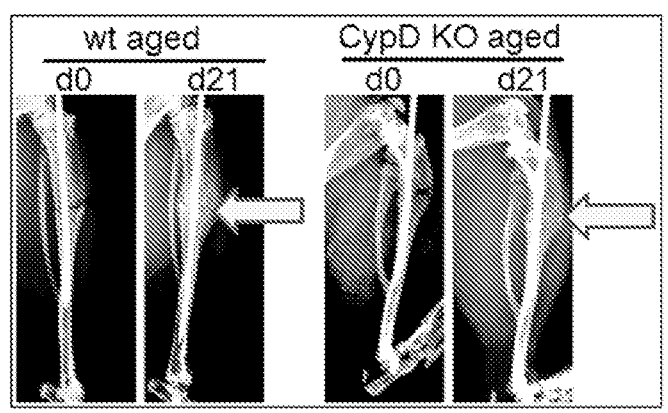
FIG. 5 shows X-ray analysis of fractured bones in aged wt and aged CypD KO mice. At day 21 post-fracture, there was no union of aged wt bone as indicated by the presence of a gap (arrow in the left panel) while there was complete union and no gap in aged CypD KO mice (arrow in the right panel). Thus, the X-ray data showed accelerated fracture healing in aged CypD KO mice when compared to the aged wt mice.

To study the effect of CypD inhibition on fracture healing in aged mice, tibial fracture of aged wt and CypD KO mice was performed and bone healing outcomes, such as bone union, bony callus formation and strength of the healed bone were evaluated. FIG. 5 shows X-ray analysis of fractured bones. At day 21 post-fracture, there was no union of aged wt bone as indicated by the presence of a gap (arrow in the left panel) while there was complete union and no gap in aged CypD KO mice (arrow in the right panel). Thus, the X-ray data showed accelerated fracture healing in aged CypD KO mice when compared to the aged wt mice.

Figure 6:
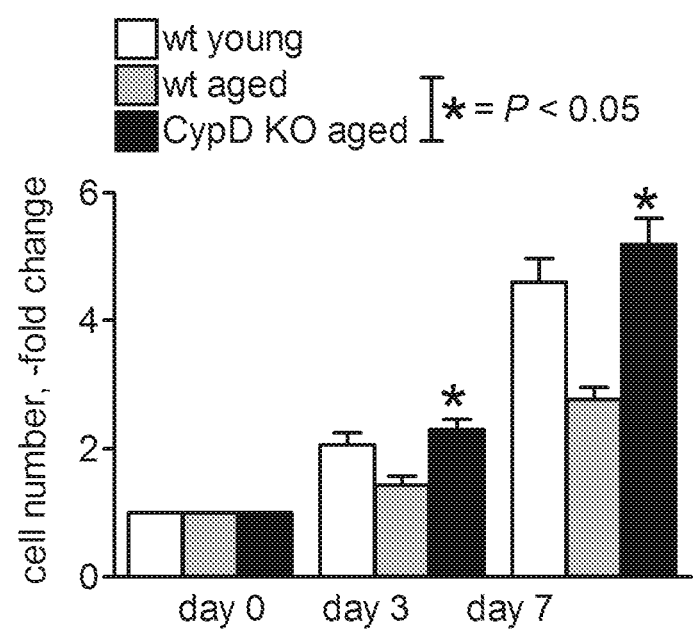
FIG. 6 shows that BM MSCs isolated from aged CypD KO mice proliferate and expand significantly faster when compared to their wt counter-parts. Data are mean+/−S.E., n=3.

Inhibition of CypD Leads to Improved Expansion Potential in Bone Marrow Mesenchymal Stem Cells As set forth above, bone marrow mesenchymal stem cells (BM MSC) isolated from aged CypD KO mice show improved mitochondrial function and osteogenicity when compared to BM MSC isolated from aged wt mice. The expansion potential of these BM MSCs was analyzed in vitro. FIG. 6 shows that BM MSCs isolated from aged CypD KO mice proliferate and expand significantly faster when compared to their wt counter-parts. Data are mean+/−S.E., n=3.

Use of Inhibitors, NIM811 and Debio025 (Alisporivir) to Treat Osteoporosis and Accelerate Fracture Healing in Aged Mice The effects of NIM811 and Deb025 (Alisporivir), on bone quality and fracture repair in aged mice can be evaluated. In the C57B6 strain, which is a background strain for both the wt and CypD KO phenotype, bone quality starts to progressively deteriorate at 11-12 months of age. By 13 months, there are significant changes in bone structure and strength, as evident from the data presented herein. To study efficacy of NIM811 and Deb025 for osteoporosis, 11 month old mice are divided in three groups and treated with either NIM811 (Group 1) or Deb025 (Group 2) or PBS as vehicle control (Group 3). The treatment regimen can be, for example, 3 mg/kg intraperitoneally (i.p.), 3 times/week. After 2 months (once the mice are 13 months of age), mouse bones are analyzed by micro-CT, histology, and biomechanical testing. Significant improvements in the treated groups (Group 1 and 2) when compared to the control group (Group 3) are expected.

To study the effect of the above compounds on fracture healing during aging, 13 month old wt mice are divided in 3 experimental groups as described above. Tibial fractures can be created in the right hind limb in each mouse using a scalpel and fixed with a metal pin inserted intramedullary. After tibial fracture, treatments can be started as described above at Day 0 until desired endpoints. Analysis will be done at day 7, 10, 14, 18, and 21 post-fracture to evaluate fracture repair outcomes, such as bone union, bony callus formation, and strength of repaired bone. X-ray, micro-CT, histology, and biomechanical testing are used to compare outcomes of fracture repair in the treated groups (Group 1 and 2) and control group (Group 3). Earlier callus formation and bone union, as well as increased strength of repaired bone in the treated groups (Group 1 and 2) are expected when compared to the control group (Group 3).

Mesenchymal Stem Cells with Reduced Expression of CypD

Provided herein are methods of treating or preventing a bone disorder by administering an effective amount of MSCs to a subject in need of treatment or prevention of a bone disorder. The MSCs are modified to reduce expression of CypD.

For example, for autologous MSC therapy, iliac crest aspiration can be performed on a patient. MSCs can be isolated from the aspirate via standard plastic adherence techniques, as described in Bianco et al. (*Nature Medicine*, 19, 35-42 (2013)), under GMP-compliant conditions. Knockdown or reduction of CypD can be performed using molecular techniques that employ shRNA, siRNA, an antisense molecule or a microRNA to decrease CypD expression. Then, MSCs can be injected into the same patient either systemically (intravenously) or locally, for example, at a fracture site.

For allogeneic MSC therapy, iliac crest aspirates can be collected from healthy donors. MSCs can be isolated as described above under GMP-compliant conditions. Knockdown or reduction of CypD can be performed as described above. Patients indicated for MSC therapy can receive either systemic or local injections of MSCs.

The MSCs can also be used for bone grafts. For example, bone autografts or allografts can be seeded (for example, as a cell suspension or on a biocompatible matrix membrane or a gel, using a cell sheet technology) with autologous or allogeneic modified MSCs, prepared as described above, before the grafting procedure. These grafts can then be transplanted in a subject.

```
CypD sequences
                                SEQ ID NO: 1
MLALRCGSRW LGLLSVPRSV PLRLPAARAC SKGSGDPSSS

SSSGNPLVYL DVDANGKPLG RVVLELKADV VPKTAENFRA

LCTGEKGFGY KGSTFHRVIP SFMCQAGDFT NHNGTGGKSI

-continued
YGSRFPDENF TLKHVGPGVL SMANAGPNTN GSQFFICTIK

TDWLDGKHVV FGHVKEGMDV VKKIESFGSK SGRTSKKIVI

TDCGQLS

SEQ ID NO: 2
gcgggactcg gccttctggg cgcgcgcgac gtcagtttga gttctgtgtt ctccccgccc gtgtcccgcc cgacccgcgc ccgcgatgct ggcgctgcgc tgcggctccc gctggctcgg cctgctctcc gtcccgcgct ccgtgccgct gcgcctcccc gcggcccgcg cctgcagcaa gggctccggc gacccgtcct cttcctcctc ctccgggaac ccgctcgtgt acctggacgt ggacgccaac gggaagccgc tcggccgcgt ggtgctggag ctgaaggcag atgtcgtccc aaagacagct gagaacttca gagccctgtg cactggtgag aagggcttcg gctacaaagg ctccaccttc cacagggtga tcccttcctt catgtgccag gcgggcgact tcaccaacca caatggcaca ggcgggaagt ccatctacgg aagccgcttt cctgacgaga actttacact gaagcacgtg gggccaggtg tcctgtccat ggctaatgct ggtcctaaca ccaacggctc ccagttcttc atctgcacca taaagacaga ctggttggat ggcaagcatg ttgtgttcgg tcacgtcaaa gagggcatgg acgtcgtgaa gaaaatagaa tctttcggct ctaagagtgg gaggacatcc aagaagattg tcatcacaga ctgtggccag ttgagctaat ctgtggccag ggtgctggca tggtggcagc tgcaaatgtc catgcaccca ggtggccgcg ttgggctgtc agccaaggtg cctgaaacga tacgtgtgcc cactccactg tcacagtgtg cctgaggaag gctgctaggg atgttagacc tcggccagga cccaccacat tgcttcctaa tacccaccct tcctcacgac ctcatttctg ggcatctttg tggacatgat gtcacccacc ccttgtcaag cattgcctgt gattgcccag cccagattca tctgtgcctt ggacatggtg atggtgatgg gttgccatcc aagtgaaagt cttttccttg accaaggggg acagtcagtt ttgcaaaagg actctaatac ctgtttaata ttgtcttcct aattgggata atttaattaa caagattgac tagaagtgaa actgcaacac taacttcccc gtgctgtggt gtgacctgag ttggtgacac aggccacaga ccccagagct tggcttttga aacacaactc agggcttttg tgaaggttcc cccgctgaga tcttttcctcc tggttactgt gaagcctgtt ggtttgctgc tgtcgttttt gagagggcc catggggta ggagcagttg aacctgggaa caaacctcac ttgagctgtg cctagacaat gtgaattcct gtgttgctaa cagaagtggc ctgtaagctc ctgtgctccg gagggaagca tttcctggta ggctttgatt tttctgtgtg
```

-continued

```
ttaaagaaat tcaatctact catgatgtgt tatgcataaa
acatttctgg aacatggatt tgtgttcacc ttaaatgtga
aaataaatcc tattttctat ggaagactgg tacctggttt
ctggaagagg ggtctgtgac ttggagctga tctttactga
gctcgccgtg gcagatgcca tgctcaggac gttcatgtgg
atggtttcat gtcatcgtgc tggcaacttg tcctcccctgc
cttagagatg aggctcagac aaacgacctt agcacccata
gcctatgcca tgagcactgg ctccaccctg aatcccagct
cctcccctta gtgacccccaa gtctgtttcc ctcagctgca
taaggaggcg atatagtttg aatatttgtc cccagccaaa
```

-continued

```
tctcatgttg aactgtaatc cccagtgctg gaggtggggc
ctgctacgag gtgtttggat catggggacg ggtatttcat
ggcttggtgc tgttttcttg atggtgaatt attgcaagat
acggtcattt aaaattgtgt ggcacctccc cctgcccct
tcttgctcct gctttcacca tgtgacatgc ctgatccccc
ttcaccttttt gccatggtca taagcttcct gaggcctccc
tggaagctga gcagatgcca gcaccatgct tcctgtacat
cctgcagaac cataagccaa ttaaacctttt ttaataataa
aaaaaaaaaa aaa
```

What is claimed is:

1. A method of treating or preventing a bone disorder in a subject, comprising administering to a subject with or at risk of developing a bone disorder an effective amount of a cyclophilin D inhibitor, wherein the bone disorder is a bone disorder associated with decreased osteogenesis, and wherein the bone disorder is osteoporosis or osteoarthritis.

2. The method of claim 1, wherein the cyclophilin D inhibitor is selected from the group consisting of N-methyl-4-isoleucine cyclosporin (NIM811), Debio 025, Sanglifehrin A, cyclosporin A and GW5.

3. The method of claim 1, wherein administration of the cyclophilin D inhibitor increases osteogenicity of mesenchymal stem cells in the subject.

4. The method of claim 1, wherein administration of the cyclophilin D inhibitor increases mitochondrial function in the subject.

5. The method of claim 1, wherein the cyclophilin D inhibitor is selected from the group consisting of N-methyl-4-isoleucine cyclosporin (NIM811), Debio 025, Sanglifehrin A, cyclosporin A and GW5.

* * * * *